(12) United States Patent
Nakajima et al.

(10) Patent No.: US 8,288,715 B2
(45) Date of Patent: Oct. 16, 2012

(54) OXYGEN DETECTION METHOD, AIR LEAKAGE DETERMINATION METHOD, GAS COMPONENT DETECTION DEVICE, AND VACUUM PROCESSING APPARATUS

(75) Inventors: Toyoaki Nakajima, Chigasaki (JP); Takeshi Miyashita, Chigasaki (JP); Yasushi Nagata, Chigasaki (JP); Yasufumi Uchida, Chigasaki (JP); Hideki Yoshizawa, Chigasaki (JP)

(73) Assignee: Ulvac, Inc., Chigasaki-Shi (JP)

( * ) Notice: Subject to any disclaimer, the term of this patent is extended or adjusted under 35 U.S.C. 154(b) by 0 days.

(21) Appl. No.: 13/125,385

(22) PCT Filed: Mar. 16, 2010

(86) PCT No.: PCT/JP2010/001860
§ 371 (c)(1),
(2), (4) Date: Apr. 21, 2011

(87) PCT Pub. No.: WO2010/106792
PCT Pub. Date: Sep. 23, 2010

(65) Prior Publication Data
US 2011/0315872 A1 Dec. 29, 2011

(30) Foreign Application Priority Data
Mar. 18, 2009 (JP) ................ P2009-066887

(51) Int. Cl.
*H01J 49/26* (2006.01)

(52) U.S. Cl. ......... 250/283; 250/282; 324/462; 324/464

(58) Field of Classification Search .......... 250/283, 250/281, 282, 427, 423 F; 324/460, 462, 324/464, 466
See application file for complete search history.

(56) References Cited

U.S. PATENT DOCUMENTS

| | | | |
|---|---|---|---|
| 2,526,038 A * | 10/1950 | Nelson | 324/466 |
| 4,620,102 A | 10/1986 | Watanabe et al. | |
| 6,635,868 B2 | 10/2003 | Shiokawa et al. | |
| 7,741,852 B2 * | 6/2010 | Watanabe et al. | 324/462 |
| 2010/0133429 A1 | 6/2010 | Nakajima et al. | |

FOREIGN PATENT DOCUMENTS

| | | |
|---|---|---|
| JP | 60-202649 | 10/1985 |
| JP | 64-010143 | 1/1989 |
| JP | 05-203524 | 8/1993 |
| JP | 6-308088 | 11/1994 |
| JP | 07-151816 | 6/1995 |

(Continued)

OTHER PUBLICATIONS

International Search Report of corresponding PCT Application No. PCT/JP2010/001860 dated Apr. 13, 2010.

*Primary Examiner* — Kiet T Nguyen
(74) *Attorney, Agent, or Firm* — Grossman, Tucker, Perreault & Pfleger, PLLC (57) ABSTRACT

An oxygen detection method, includes: preparing a grid, an ion collector, and a filament in which an oxide are formed on a surface of metal; controlling a filament current flowing to the filament so that an emission current becomes constant; discharging thermionic electrons which are caused by heat generation by applying the filament current, and generating ions by ionizing a gas; capturing the ions with the ion collector; and detecting oxygen being present in a vacuum processing chamber by measuring a filament current value.

11 Claims, 4 Drawing Sheets

FOREIGN PATENT DOCUMENTS

| | | |
|---|---|---|
| JP | 10-213508 | 8/1998 |
| JP | 2001-273869 | 10/2001 |
| JP | 2003-185635 | 7/2003 |
| JP | 2005-114388 | 4/2005 |
| JP | 2005-259606 | 9/2005 |
| JP | 2006-329662 | 12/2006 |
| JP | 2007-335188 | 12/2007 |
| JP | 2008-209181 | 9/2008 |
| WO | 2008/010887 | 1/2008 |
| WO | 2008/133074 | 11/2008 |

* cited by examiner

OXYGEN DETECTION METHOD, AIR LEAKAGE DETERMINATION METHOD, GAS COMPONENT DETECTION DEVICE, AND VACUUM PROCESSING APPARATUS

CROSS-REFERENCE TO RELATED APPLICATIONS

This is the U.S. National Phase Application under 35 U.S.C. §371 of International Patent Application No. PCT/JP2010/001860 filed Mar. 16, 2010, which designated the United States and was published in a language other than English, which claims the benefit of Japanese Patent Application No. 2009-066887 filed on Mar. 18, 2009, both of them are incorporated by reference herein. The International Application was published in Japanese on Sep. 23, 2010 as WO2010/106792 A1 under PCT Article 21(2).

BACKGROUND OF THE INVENTION

1. Field of the Invention

The present invention relates to an oxygen detection method, an air leakage determination method, a gas component detection device, and a vacuum processing apparatus.

Particularly, the invention relates to a method of efficiently detecting oxygen inside a vacuum processing chamber by controlling and measuring a filament current using an ionization vacuum gauge or a mass spectrometer, a method of determining a leakage of air, a gas component detection device used to perform the detection method or the determination method, and a vacuum processing apparatus including the gas component detection device.

2. Background Art

Conventionally, a hot cathode ionization vacuum gauge has been widely used to measure a pressure (a vacuum degree) inside a vacuum processing chamber of the vacuum processing apparatus used in a manufacturing device for a semiconductor, a flat panel display, a solar cell, or the like.

Figure 6:
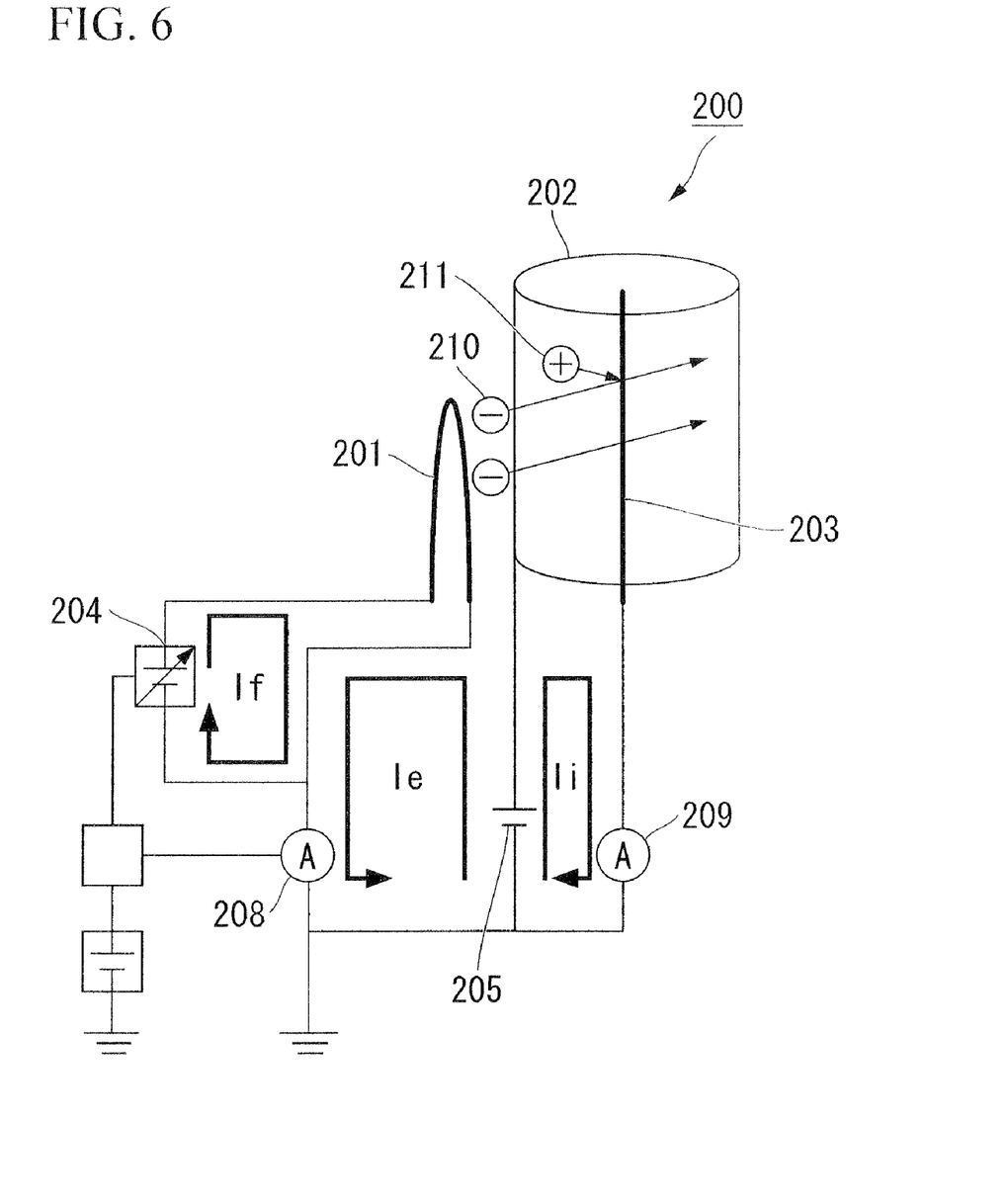
FIG. 6 is a schematic diagram illustrating an example of a conventional hot cathode ionization vacuum gauge.

FIG. 6 is a schematic diagram illustrating a configuration of a conventional hot cathode ionization vacuum gauge.

In a conventional hot cathode ionization vacuum gauge 200, one end of a filament 201 is connected to a plus terminal of a variable power source 204.

Additionally, the other end of the filament 201 is connected to a minus terminal of the variable power source 204, and is grounded through an emission current meter 208.

The filament 201 is disposed in the vacuum atmosphere together with a grid 202 and an ion collector 203.

The grid 202 is connected to a plus terminal of a grid bias power source 205.

In the hot cathode ionization vacuum gauge 200, in accordance with the activation of the variable power source 204, the filament current If flows to the filament 201, the filament 201 emits heat, and thermionic electrons 210 are discharged.

The thermionic electrons 210 discharged from the filament 201 arrive at the grid 202, thereby generating an emission current Ie.

Furthermore, gas molecules are ionized since the thermionic electrons 210 collide with the gas molecules before the thermionic electrons 210 arrive at the grid 202, thereby generating positive ions 211.

The positive ions 211 generated at this time are collected at the ion collector 203, thereby generating an ion current Ii.

The density of a gas, that is, a vacuum degree is measured by measuring the emission current Ie and the ion current Ii.

That is, it is known that the following equation (1) is established by a pressure P, an ion current Ii, and an emission current Ie.

Here, S indicates a sensitivity coefficient.

Equation (1)

$$P = Ii/(S \cdot Ie) \quad (1)$$

Accordingly, when the output value of the variable power source 204 is changed and the filament current If is controlled so that emission current Ie becomes constant, the pressure P can be calculated.

In addition, conventionally, a method of measuring a filament current value and estimating durability of a filament by using this value has been known (for example, refer to Japanese Unexamined Patent Application, First Publication No. H7-151816).

Moreover, a method of preventing a filament from being disconnected has been known (for example, refer to Japanese Unexamined Patent Application, First Publication No. S64-10143).

Furthermore, a method of using a measurement value of a current applied to a filament in order to calculate correct values of sensitivity and display pressure has been known (for example, refer to Japanese Unexamined Patent Application, First Publication No. H5-203524).

However, in order to determine whether a leakage occurs in the vacuum apparatus, it is necessary to perform any one of a method of measuring a leakage amount in accordance with a build-up technique using an ionization vacuum gauge, a method of monitoring a partial pressure of a gas using a mass spectrometer, and a method of performing a helium leakage test in a manner such that a helium gas is sprayed to a surface of a vacuum apparatus and the helium gas passing through the leakage portion is detected (for example, refer to Japanese Unexamined Patent Application, First Publication No. 2006-329662).

However, since the build-up technique is dependent on the state of the apparatus, accurate determination is difficult to perform.

Additionally, in the method of using the mass spectrometer, the mass spectrometer is expensive and the portably is poor.

Furthermore, when the pressure of the vacuum apparatus is greater than or equal to 0.1 Pa, the mean free path of the gas becomes short.

For this reason, in the method of using the mass spectrometer, there are problems in that a signal relative to a mass-to-charge ratio starts to remarkably decrease and almost no signal is detected when the pressure of the vacuum apparatus is greater than or equal to 1 Pa (for example, refer to Japanese Unexamined Patent Application, First Publication No. 2008-209181).

On the other hand, there is also proposed a mass spectrometer capable of performing a measurement in a wide pressure region (for example, refer to Japanese Unexamined Patent Application, First Publication No. 2007-335188).

Many vacuum processing apparatuses running presently are mounted with the ionization vacuum gauge or the mass spectrometer described above.

For this reason, when the presence of oxygen and the leakage of air can be detected by using an existing ionization vacuum gauge or an existing mass spectrometer as necessary, the convenience greatly improves.

SUMMARY OF THE INVENTION

The present invention is made in view of such circumstances, and an object thereof is to provide a method of detecting oxygen inside a vacuum processing chamber in a manner such that oxygen inside the vacuum processing chamber is detected by using an ionization vacuum gauge or a mass spectrometer used in a vacuum processing apparatus in many cases, whereby a detection unit need not be further installed, costs can be reduced, and an installation space can be reduced.

In order to solve the above-described problems, an oxygen detection method of a first aspect of the invention includes: preparing a grid, an ion collector, and a filament in which an oxide are formed on a surface of metal; controlling a filament current flowing to the filament so that an emission current becomes constant; discharging thermionic electrons which are caused by heat generation by applying the filament current, and generating ions by ionizing a gas; capturing the ions with the ion collector; and detecting oxygen being present in a vacuum processing chamber by measuring a filament current value.

It is preferable that the oxygen detection method of the first aspect of the invention further include using an ionization vacuum gauge including the filament and the grid.

It is preferable that the oxygen detection method of the first aspect of the invention further include using a mass spectrometer including the filament and the grid.

In the oxygen detection method of the first aspect of the invention, it is preferable that, the metal be iridium and the oxide be yttrium oxide.

An air leakage determination method of a second aspect of the invention determines whether a leakage of air is present using the oxygen detection method of the first aspect of the invention.

A gas component detection device of a third aspect of the invention carries out the oxygen detection method of the first aspect of the invention.

It is preferable that the gas component detection device of the third aspect of the invention further include an output unit outputting, to an exterior, a filament current value, a pressure value, and an oxygen detection signal.

A gas component detection device of a fourth aspect of the invention carries out the air leakage determination method of the second aspect of the invention.

It is preferable that the gas component detection device of the fourth aspect of the invention further include an output unit outputting, to an exterior, a filament current value, a pressure value, and an oxygen detection signal.

A vacuum processing apparatus of a fifth aspect of the invention includes the gas component detection device of the third aspect of the invention.

A vacuum processing apparatus of a sixth aspect of the invention includes the gas component detection device of the fourth aspect of the invention.

ADVANTAGEOUS EFFECTS OF INVENTION

According to the oxygen detection method of the invention, a grid, an ion collector, and a filament in which oxides are coated on a surface of metal (a base material) are used, a filament current flowing to the filament is controlled so that an emission current becomes constant, and the filament current is measured.

Accordingly, oxygen present inside the vacuum processing chamber can be detected, and the leakage of air can be detected.

Therefore, it is possible to determine whether oxygen is present inside the vacuum processing chamber and air leaks by using a hot cathode ionization vacuum gauge or a mass spectometer used in many vacuum processing apparatuses.

Accordingly, a detection unit need not be further installed, costs can be reduced, and an installation space can be reduced.

Particularly, when the mass spectrometer is used, even in the pressure region in which a signal with respect to a mass-to-charge ratio greatly decreases, it is possible to determine whether oxygen is present and air leaks.

Accordingly, the convenience of the mass spectrometer remarkably improves.

Therefore, even when any one of the ionization vacuum gauge and the mass spectrometer is used, it is possible to determine whether oxygen is present inside the vacuum processing chamber and air leaks. Accordingly, the further convenience can be obtained by separately using any one of the ionization vacuum gauge and the mass spectrometer as necessary.

DESCRIPTION OF THE PREFERRED EMBODIMENTS

Hereinafter, an embodiment of an oxygen detection method and an air leakage determination method according to the invention will be described.

In the respective drawings used in the description below, in order to make the respective components be of understandable size in the drawing, the dimensions and the proportions of the respective components are modified as needed compared with the real components.

Figure 1:
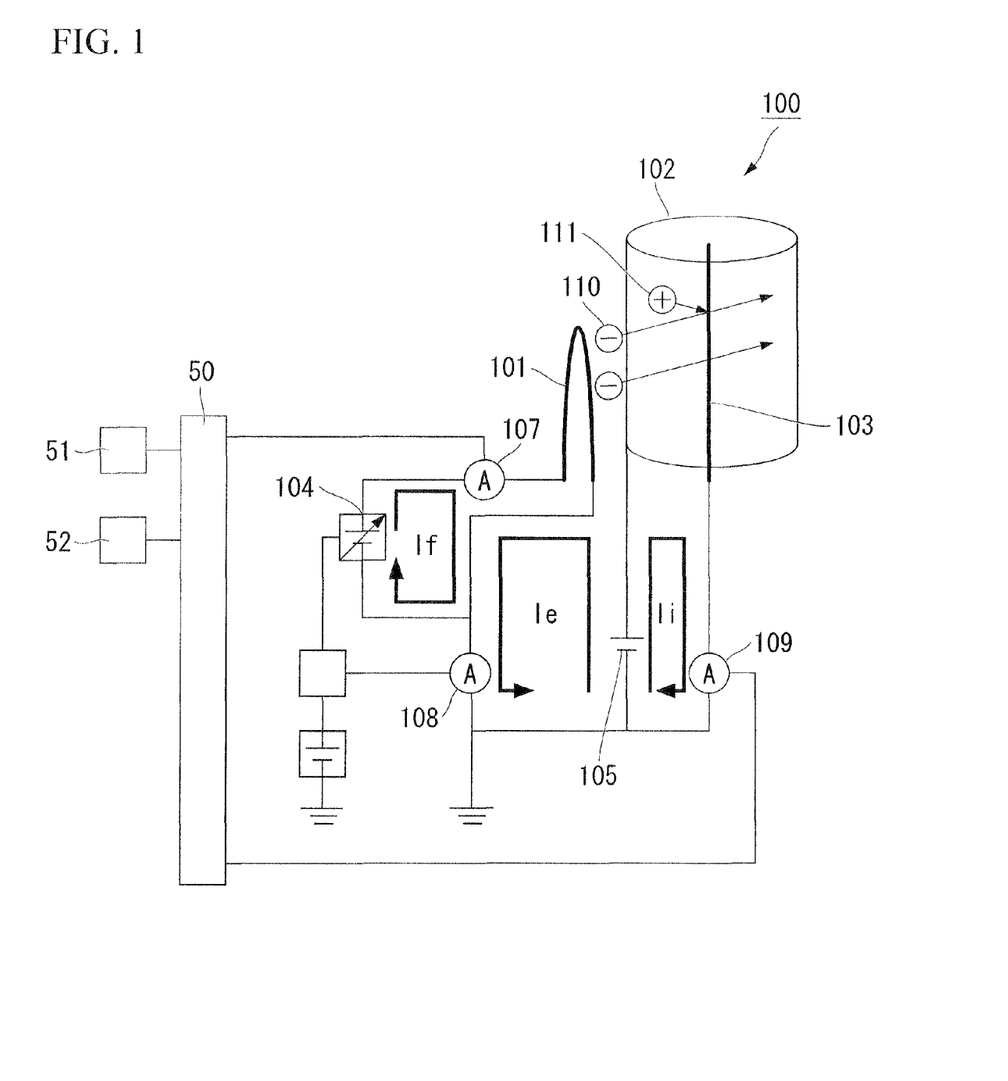
FIG. 1 is a schematic diagram illustrating a configuration of a gas component detection device according to the invention.

FIG. 1 is a schematic diagram illustrating a basic configuration of a gas component detection device 100 (ionization vacuum gauge) using the oxygen detection method and the air leakage determination method according to the invention.

The gas component detection device 100 includes a filament 101, a grid 102, an ion collector 103, a variable power source 104, a grid bias power source 105, a filament current meter 107, an emission current meter 108, and an ion current meter 109.

The filament 101, the grid 102, and the ion collector 103 are disposed in the atmosphere inside a vacuum processing chamber of a vacuum processing apparatus.

In the gas component detection device 100, one end of the filament 101 is connected to a plus terminal of the variable power source 104 through the filament current meter 107.

Additionally, the filament current meter 107 and the ion current meter 109 are electrically connected to an output unit 50 that outputs a signal to a measurement device 51 or a control device 52.

Accordingly, a value measured in the filament current meter 107 and the ion current meter 109 is output to the measurement device 51 or the control device 52 through the output unit 50.

Furthermore, the measurement device 51 or the control device 52 constitutes a part of the vacuum processing apparatus.

The measurement device 51 or the control device 52 includes a storage unit that stores a value measured in the filament current meter 107 and the ion current meter 109.

The storage unit stores a pressure and a filament current value as described below.

With this configuration, a pressure and a filament current value inside the vacuum processing chamber when various gases are introduced into the vacuum processing chamber can be recorded and stored.

Moreover, the gas component detection device 100 provided with the ionization vacuum gauge is shown in FIG. 1, but the same configuration is adopted even when a mass spectrometer is used instead of the ionization vacuum gauge.

EXPERIMENTAL EXAMPLE 1

In this example, a gas was introduced into the vacuum processing chamber while a high vacuum atmosphere was obtained inside the vacuum processing chamber, and a relationship between a measured pressure P and a measured filament current If was examined.

As the gas, nitrogen used for a general vent operation, air detected separately from nitrogen, and oxygen were respectively selected.

Figure 2:
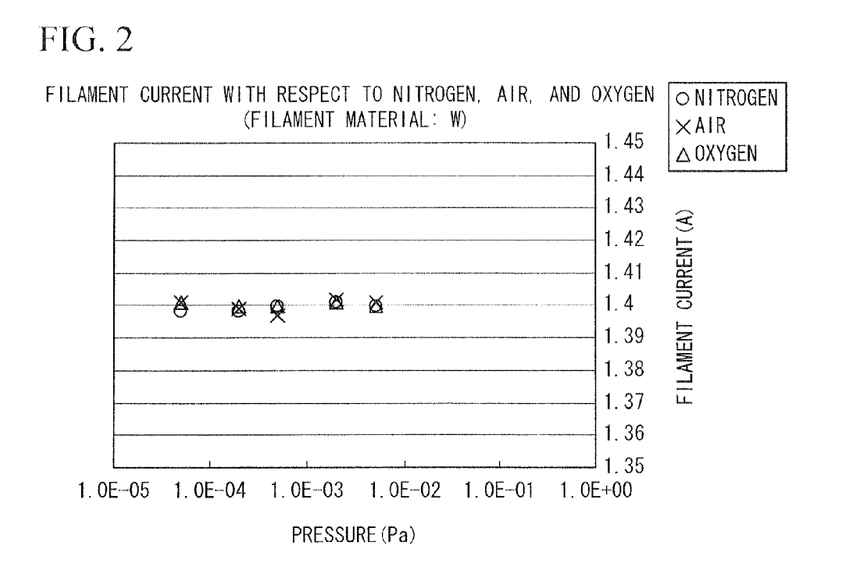
FIG. 2 is a diagram illustrating a relationship between a pressure and a filament current value when various gases are introduced in the case of using a conventional filament.
Figure 3:
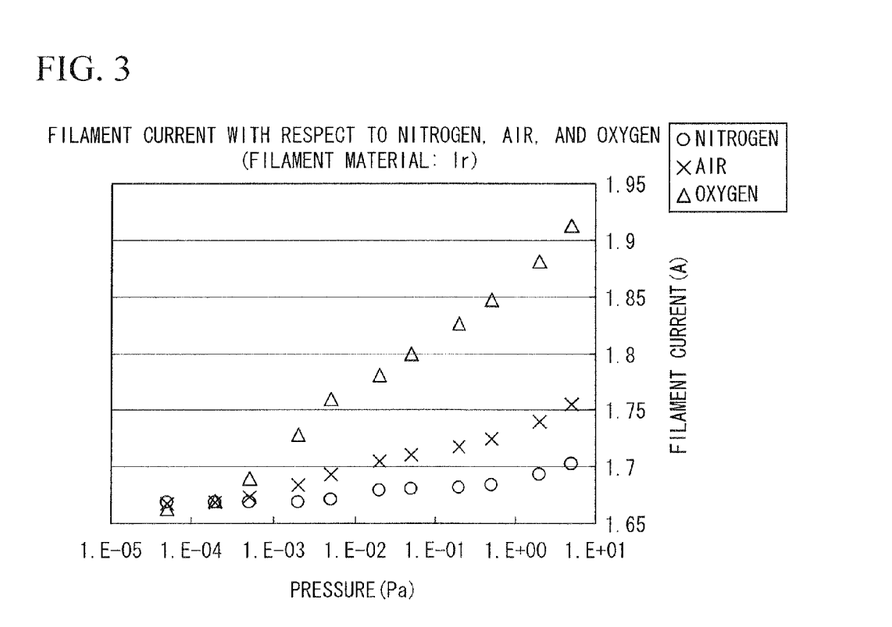
FIG. 3 is a diagram illustrating a relationship between a pressure and a filament current value when various gases are introduced in the case of using a filament according to the invention.

In FIGS. 2 and 3 to be described below, the horizontal axis indicates a pressure P, and the vertical axis indicates a filament current If.

FIG. 2 illustrates a comparison result between the pressure P and the filament current If when nitrogen, air, and oxygen are introduced by using the gas component detection device 100 using tungsten (W) which has been used as a material of the filament 101 for some time.

As shown in FIG. 2, in the relationship between the pressure P and the filament current If, no difference was found between nitrogen, air, and oxygen.

Therefore, the type of gas introduced into the vacuum processing chamber cannot be determined.

On the contrary, FIG. 3 illustrates a comparison result between the pressure P and the filament current If when nitrogen, air, and oxygen are introduced by using the gas component detection device 100 using the filament 101 having a structure in which oxides are coated on a surface of a metallic base material.

Specifically, the filament 101 is used in which yttrium oxide ($Y_2O_3$) is coated on a surface of a base material of iridium (Ir), and a result obtained by the same test as that of FIG. 2 is shown.

From the result shown in FIG. 3, the following points become apparent.

(Result 1) The filament current If measured when introducing air is greater than the filament current If measured when introducing nitrogen.

(Result 2) The filament current If measured when introducing oxygen is much greater than the filament current If measured when introducing air.

(Result 3) Result 2 is obtained when the pressure (Pa) is in a pressure area of $5 \times 10^{-4}$ or more.

(Result 4) When the pressure (Pa) is in a pressure area of $5 \times 10^{-4}$ or more, the detected gas can be determined as any one of nitrogen, air and oxygen.

Moreover, since there is a tendency that a difference in the filament current If of nitrogen and air and a difference in the filament current If of air and oxygen increase as a pressure increases, the precision of detecting the type of gas improves.

Therefore, when the type of gas is detected by using the filament having a configuration shown in FIG. 3, that is, a structure in which oxides are coated on the surface of the metallic base material, the type of the gas present inside the vacuum processing chamber can be reliably determined.

Generally, the number of electrons flying out from a surface of metal per the unit of area and time (thermionic electron emission current density) J are expressed by the following equation (2) (Richardson-Dushman equation).

Equation (2)

$$J = AT^2 \exp(-\phi/(kT)) \quad (2)$$

Here, k indicates a Boltzmann constant, Φ indicates a work function, A indicates a Richardson constant, $A = 4\pi mk^2 e/h^3$, m and e respectively indicate mass and electric charge of an electron, h indicates a Frank constant, and T indicates temperature.

As understood from the equation (2), the number of thermionic electrons decreases when the work function is large, and the number of thermionic electrons increases when the temperature increases.

Additionally, the filament current increases when the pressure increases since the quantity of heat taken out of the filament increases.

Therefore, the amount of the filament current is dependent on the pressure (for example, refer to Japanese Unexamined Patent Application, First Publication No. H7-151816).

In FIG. 3, a result is obtained in which the filament current If measured when introducing oxygen is greater than the filament current If measured when introducing air (Result 2).

Also, even under the same pressure, the filament current If of oxygen becomes greater than the filament current If of air.

The reason is considered as below. When oxygen is absorbed onto the surface of the filament, electrons are taken out of the surface of the filament, and negative oxygen ions are absorbed onto the surface of the filament. Accordingly, the work function increases, so that the filament current for obtaining the stipulated emission current increases (the temperature thereof increases).

(First Detection Method)

In the gas component detection device 100 of FIG. 1, the pressure and the filament current value when introducing nitrogen into the vacuum processing chamber are recorded and stored in advance as reference values.

Subsequently, a filament current value is measured when an uncertain type of gas is introduced into the vacuum processing chamber, and the reference value and the measurement value are compared with each other, thereby detecting the presence of air or oxygen inside the vacuum processing chamber.

That is, a nitrogen gas (a reference gas and a first gas) as a reference is introduced into the vacuum processing chamber, and a filament current (a first filament current) is measured.

Subsequently, the measured filament current value is stored as a reference value.

Subsequently, an uncertain type of gas (a measurement target gas and a second gas) is introduced into the vacuum processing chamber, and a filament current value (a second filament current) is measured.

Subsequently, the reference value and the filament current value of the uncertain type of gas are compared with each other.

Accordingly, it is possible to detect whether the uncertain type of gas present inside the vacuum processing chamber is oxygen or air.

Therefore, the method of the invention can be effectively used as a method of determining the leakage of air inside the vacuum processing chamber.

(Second Detection Method)

Furthermore, in the detection method of the invention, when it is determined that the filament current value of the gas introduced into the vacuum current value is a specified value or more in a predetermined pressure, the uncertain type of gas present inside the vacuum processing chamber may be determined to be oxygen or air.

Specifically, a characteristic (a first characteristic) representing a relationship between the pressure and the filament current when introducing oxygen into the vacuum current chamber is stored, and a characteristic (a second characteristic) representing a relationship between the pressure and the filament current when introducing air into the vacuum processing chamber is stored.

That is, the relationship between the pressure and the filament current shown in FIG. 3 is stored.

Accordingly, a specified value (a first specified value) of oxygen and a specified value (a second specified value) of air are decided.

Next, when it is determined that a filament current value measured at a predetermined pressure when introducing an uncertain type of gas into the vacuum processing chamber is greater than or equal to a first specified value, the uncertain type of gas present inside the vacuum processing chamber is determined to be oxygen.

Additionally, when it is determined that a filament current value measured at a predetermined pressure is greater than or equal to a second specified value, the uncertain type of gas present inside the vacuum processing chamber is determined to be air.

(Third Detection Method)

Furthermore, in the method of the invention, the gas introduced into the vacuum processing chamber may be determined to be oxygen or air on the basis of the difference between the above-described reference value and the measurement value of the uncertain type of gas.

Specifically, the filament current value (the first filament current) measured when introducing nitrogen into the vacuum processing chamber is determined as the reference value.

Furthermore, the first specified value (oxygen) and the second specified value (air) are determined on the basis of the above-described first and second characteristics.

Next, a first difference value obtained by subtracting the reference value from the first specified value and a second difference value obtained by subtracting the reference value from the second specified value are calculated and stored.

Next, when it is determined that a filament current value measured when introducing an uncertain type of gas into the vacuum processing chamber is greater than or equal to the first difference value, the uncertain type of gas present inside the vacuum processing chamber is determined to be oxygen.

Additionally, when it is determined that a filament current value measured when introducing an uncertain type of gas into the vacuum processing chamber is greater than or equal to the second difference value, the uncertain type of gas present inside the vacuum processing chamber is determined to be air.

Moreover, for example, in a sputtering apparatus, a film forming process may be performed at the atmosphere in which oxygen is introduced in addition to argon.

Even in this case, the pressure and the filament current value measured when introducing argon and oxygen used for a film forming process into the vacuum processing chamber in advance are recorded and stored as reference values.

However, when the filament is used in which yttrium oxide ($Y_2O_3$) or the like is coated on a surface of a base material of iridium (Ir), the filament is degraded and the filament current gradually increases by increasing the frequency in use (for example, refer to Japanese Unexamined Patent Application, First Publication No. H7-151816).

In this case, it is desirable that the pressure and the filament current value when introducing nitrogen into the vacuum processing chamber be measured and the reference value be set again.

In addition, the pressure and the filament current value when introducing nitrogen into the vacuum processing chamber may be stored in a storage device inside the ionization vacuum gauge.

Additionally, an oxygen detection signal or an air leakage determination signal may be output to the output unit 50.

EXPERIMENTAL EXAMPLE 2

Figure 4:
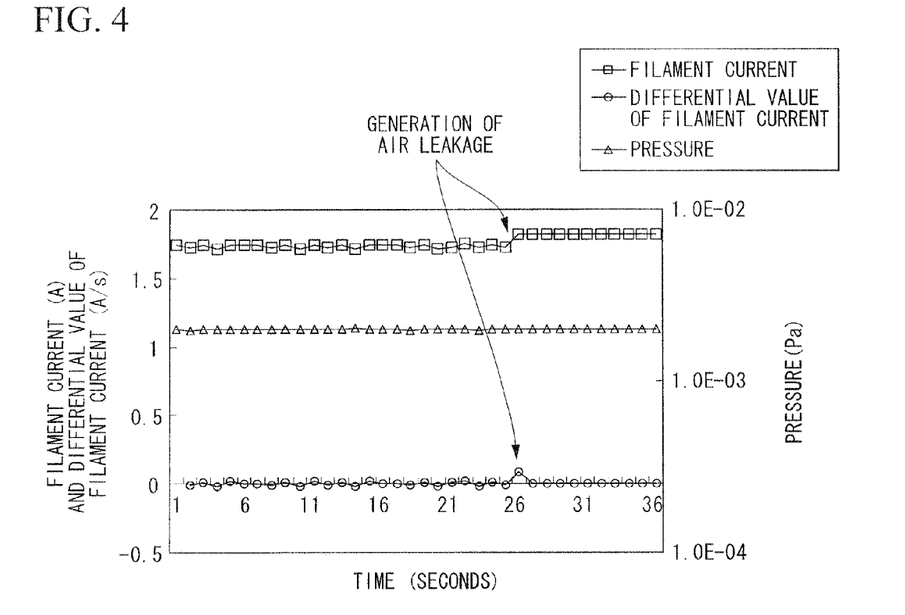
FIG. 4 is a diagram illustrating a pressure inside a vacuum processing chamber, a filament current, and a temporal variation in the differential value of the filament current.

FIG. 4 is a diagram illustrating a temporal variation of the pressure and the filament current value measured in accordance with the above-described method.

In FIG. 4 to be described below, the horizontal axis indicates the time, and the vertical axis indicates the filament current If and the differential value of the filament current.

As shown in FIG. 4, it is found that the filament current value increases at the time when approximately 26 seconds have elapsed.

At the same time, it is apparent that the filament current value changes at the differential value of the filament current value.

That is, when it is detected that the pressure measured by the ionization vacuum gauge does not change and the differential value of the filament current is greater than or equal to a specified value, it is possible to determine air being present inside the vacuum processing chamber.

That is, it is possible to determine the abrupt leakage of air occurs.

In this case, since it is not necessary to record and store in advance the reference value when introducing nitrogen into the vacuum processing chamber, it is possible to reduce an adverse effect in which the filament current gradually decreases due to the deterioration of the filament.

EXPERIMENTAL EXAMPLE 3

Recently, a vacuum gauge has been known in which an ionization vacuum gauge and a Pirani gauge that can be measured from the atmospheric pressure are assembled in the same vacuum processing chamber.

This vacuum gauge has a structure in which the pressure inside the vacuum processing chamber is measured by the Pirani gauge in the range from the atmospheric pressure to the pressure that can be detected by the ionization vacuum gauge, and the filament is automatically turned on when the pressure inside the vacuum processing chamber arrives at a pressure p1 (a measurable pressure p1) at which the pressure inside the vacuum processing chamber can be measured by the ionization vacuum gauge.

Figure 5:
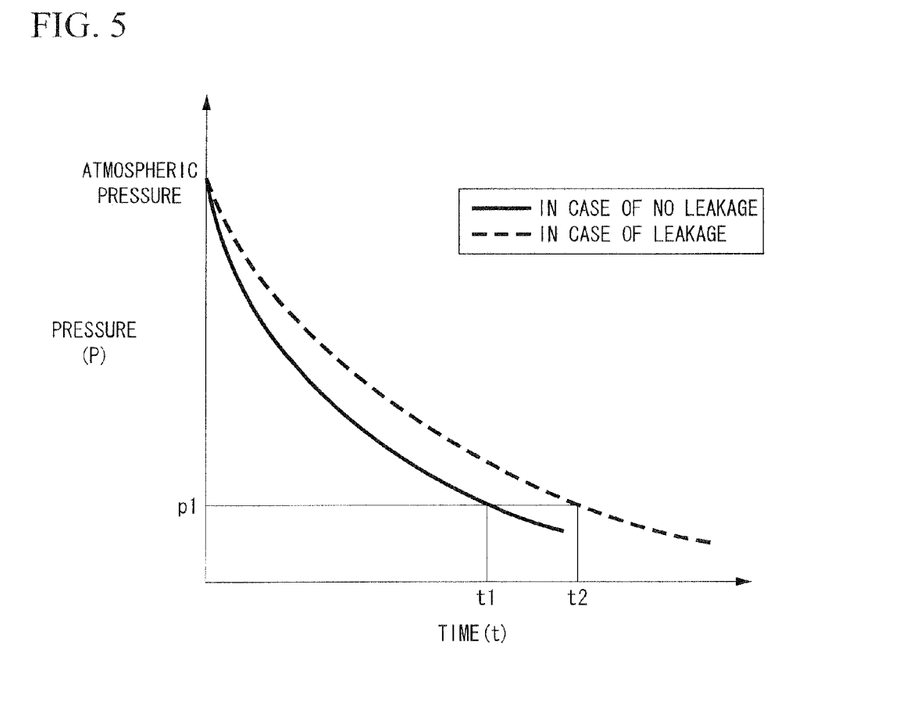
FIG. 5 is a diagram illustrating a relationship between a pressure and a time when a vacuum processing chamber is depressurized.

FIG. 5 is a diagram illustrating a relationship between a pressure and a time necessary for depressurization when the vacuum processing chamber is depressurized from an atmospheric pressure to a vacuum.

The time necessary from the start of the depressurization to the arrival of the measurable pressure p1 is determined as the reference.

When there is no leakage of air inside the vacuum processing chamber, a time t1 (a reference time) at which the filament is turned on and a filament current a1 (a reference current) at the time t1 are recorded in advance.

As the number of times of performing a process (for example, a film forming process) using the vacuum processing chamber increases and the number of times of maintenance of the vacuum processing chamber increases, the possibility of generating leakage inside the vacuum processing chamber increases.

For this reason, there is a need to detect the leakage state.

Experimental Example 3 indicates an example in which the leakage state is detected in such a case as this.

As shown in FIG. 5, when the time necessary from the start of depressurization to the arrival of the measurable pressure p1, that is, the time t2 necessary from the start of depressurization to the activation of the filament is longer than the time t1, it is suspected that air leakage occurs inside the vacuum processing chamber.

When the filament current value a2 at this time is greater than the filament current value a1, it is possible to determine occurrence of the leakage of air.

However, when the current value a2 is equal to the current value a1, it is possible to determine occurrence of the leakage due to other reasons such as a vacuum pump abnormality.

In this manner, when the value of the filament current is monitored, the leakage of air can be more accurately determined.

Therefore, according to the invention, it is possible to determine whether oxygen is present inside the vacuum processing chamber and air leaks by using a hot cathode ionization vacuum gauge used in many vacuum processing apparatuses.

Accordingly, a detection unit need not be further installed, costs can be reduced, and an installation space can be reduced.

Additionally, even when the mass spectrometer is used, the filament current value may be measured by using a mass spectrometer having a voltmeter assembled therein (for example, refer to Japanese Unexamined Patent Application, First Publication No. 2007-335188).

With this configuration, even in the pressure region in which a signal with respect to a mass-to-charge ratio greatly decreases, it is possible to determine whether oxygen is present and air leaks in accordance with a similar method as that described in Experimental Examples 1 to 3.

Accordingly, the convenience of the mass spectrometer remarkably improves.

Moreover, in Experimental Examples 1 to 3, a case has been described in which the filament current is a direct current, but the filament current If flowing to the filament need not essentially be a direct current in order to emit thermionic electrons.

For example, a structure (a circuit) in which an alternate current or a conduction angle is controlled may be used.

In this structure, when the emission current Ie is maintained at a desired magnitude by controlling the filament current If, the effective value of the filament current If may be measured, and whether oxygen is present and air leaks may be determined by detecting the effective value.

Additionally, in Experimental Examples 1 to 3, a case is described in which the detected gas is oxygen and air, but the invention is not limited to such a detection method.

For example, electrons may be taken out of the filament to increase the work function, and water ($H_2O$) or the like containing oxygen atoms may be detected.

On the other hand, when a reducing gas such as hydrogen is absorbed to the filament, electrons move from the gas to the surface of the filament, and positive hydrogen ions are absorbed to the surface of the filament, whereby the work function decreases, and then the filament current decreases.

By utilizing this phenomenon, hydrogen can be detected.

As described above, by only using a configuration in which the ionization vacuum gauge or the mass spectrometer including the filament in which oxides are coated on the surface of the metallic base material, and the filament current value is measured, it is possible to determine whether oxygen is detected and air leaks.

Therefore, according to the invention, even when any one of the ionization vacuum gauge and the mass spectrometer is used, it is possible to determine whether oxygen is detected inside the vacuum processing chamber and air leaks by appropriately using the ionization vacuum gauge or the mass spectrometer in accordance with the state in which the vacuum processing apparatus is used. Accordingly, convenience may improve.

The technical scope of the invention is not limited to the above-described embodiment, and may be modified into various forms within the scope of the invention.

Additionally, the invention is not limited to the ionization vacuum gauge or the mass spectrometer, and may be applied to a device (vacuum gauge) having a configuration corresponding to a filament and a grid.

INDUSTRIAL APPLICABILITY

The invention can be widely used in a method of detecting a gas component such as air and oxygen inside a vacuum processing chamber using an ionization vacuum gauge or a mass spectrometer including a filament in which oxides are disposed on a surface of metal, and a device for detecting a gas component such as air or oxygen.

What is claimed is:
1. An oxygen detection method, comprising:
preparing a grid, an ion collector, and a filament in which an oxide are formed on a surface of metal;
controlling a filament current flowing to the filament so that an emission current becomes constant;
discharging thermionic electrons which are caused by heat generation by applying the filament current, and generating ions by ionizing a gas;
capturing the ions with the ion collector; and
detecting oxygen being present in a vacuum processing chamber by measuring a filament current value.

2. The oxygen detection method according to claim 1, further comprising:
using an ionization vacuum gauge including the filament and the grid.

3. The oxygen detection method according to claim 1, further comprising:
using a mass spectrometer including the filament and the grid.

4. The oxygen detection method according to claim 1, wherein the metal is iridium, and the oxide is yttrium oxide.

5. An air leakage determination method determining whether a leakage of air is present using the oxygen detection method according to claim 1.

6. A gas component detection device carrying out the air leakage determination method according to claim 5.

7. The gas component detection device according to claim 6 further comprising an output unit outputting, to an exterior, a filament current value, a pressure value, and an oxygen detection signal.

8. A vacuum processing apparatus comprising the gas component detection device according to claim 6.

9. A gas component detection device carrying out the oxygen detection method according to claim 1.

10. The gas component detection device according to claim 9 further comprising an output unit outputting, to an exterior, a filament current value, a pressure value, and an oxygen detection signal.

11. A vacuum processing apparatus comprising the gas component detection device according to claim 9.

* * * * *